(12) United States Patent
Klemm

(10) Patent No.: US 11,141,532 B2
(45) Date of Patent: Oct. 12, 2021

(54) MONITORING DEVICE FOR ATTACHMENT TO AN INJECTION DEVICE

(71) Applicant: SANOFI-AVENTIS DEUTSCHLAND GMBH, Frankfurt am Main (DE)

(72) Inventor: Thomas Klemm, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 120 days.

(21) Appl. No.: 16/482,428

(22) PCT Filed: Jan. 31, 2018

(86) PCT No.: PCT/EP2018/052334
§ 371 (c)(1),
(2) Date: Jul. 31, 2019

(87) PCT Pub. No.: WO2018/141764
PCT Pub. Date: Aug. 9, 2018

(65) Prior Publication Data
US 2019/0358402 A1   Nov. 28, 2019

(30) Foreign Application Priority Data
Feb. 1, 2017 (EP) .................................... 17154215

(51) Int. Cl.
*A61M 5/315* (2006.01)
*A61M 5/24* (2006.01)

(52) U.S. Cl.
CPC .......... *A61M 5/24* (2013.01); *A61M 5/31568* (2013.01); *A61M 2205/3306* (2013.01);
(Continued)

(58) Field of Classification Search
CPC .. A61M 5/1411; A61M 5/1689; A61M 5/162; A61M 5/40; A61M 5/31568
See application file for complete search history.

(56) References Cited

U.S. PATENT DOCUMENTS

| | | | | | |
|---|---|---|---|---|---|
| 4,261,388 | A | * | 4/1981 | Shelton | A61M 5/1689 137/486 |
| 4,533,350 | A | * | 8/1985 | Danby | A61M 5/1689 604/253 |
| 4,673,820 | A | * | 6/1987 | Kamen | G06M 11/00 250/573 |

FOREIGN PATENT DOCUMENTS

| | | |
|---|---|---|
| CN | 105167781 | 12/2015 |
| CN | 105377328 | 3/2016 |

(Continued)

OTHER PUBLICATIONS

International Preliminary Report on Patentability in Application No. PCT/EP2018/052334, dated. Aug. 6, 2019, 7 pages.
(Continued)

*Primary Examiner* — Manuel A Mendez
(74) *Attorney, Agent, or Firm* — Fish & Richardson P.C.

(57) ABSTRACT

In one aspect the present disclosure relates to a monitoring device for attachment to an injection device, the monitoring device comprising:
a body (51) having an inside surface (52) for engagement with an outside surface (19) of the injection device (1) and having an outside surface (53) opposite to the inside surface (52),
an light transmission area (60) extending from the inside surface (52) to the outside surface (53), the light transmission area (60) having an inner end (62) adjacent to the inside surface and having an outer end (63) adjacent to the outside surface (52), wherein the light transmission area (60) provides transmission of light from the inner end (62) to the outer end (63),
an image acquisition system (70) arranged inside or on the body (51), and
an optical coupling (80) arranged in or extending into the light transmission area (60), wherein the optical cou-
(Continued)

pling (80) is optically coupled to the image acquisition system (70) in a light-transmitting way.

20 Claims, 6 Drawing Sheets

(52) U.S. Cl.
 CPC .......... *A61M 2205/3561* (2013.01); *A61M 2205/505* (2013.01); *A61M 2205/52* (2013.01); *A61M 2205/581* (2013.01); *A61M 2205/582* (2013.01); *A61M 2205/8206* (2013.01)

(56) References Cited

FOREIGN PATENT DOCUMENTS

| CN | 205658923 | 10/2016 | |
|---|---|---|---|
| EP | 1839693 | 10/2007 | |
| WO | WO 2006/120182 | 11/2006 | |
| WO | WO 2011/117212 | 9/2011 | |
| WO | WO 2013/004843 | 1/2013 | |
| WO | WO 2013/120775 | 8/2013 | |
| WO | WO 2014/152704 | 9/2014 | |
| WO | WO 2015/001008 | 1/2015 | |
| WO | WO 2015/189170 | 12/2015 | |
| WO | WO-2015189170 A1 * | 12/2015 | ............ A61M 5/168 |

OTHER PUBLICATIONS

International Search Report and Written Opinion in Application No. PCT/EP2018/052334, dated Apr. 19, 2018, 10 pages.

* cited by examiner

MONITORING DEVICE FOR ATTACHMENT TO AN INJECTION DEVICE

CROSS REFERENCE TO RELATED APPLICATIONS

The present application is the national stage entry of International Patent Application No. PCT/EP2018/052334, filed on Jan. 31, 2018, and claims priority to Application No. EP17154215.2, filed on Feb. 1, 2017 the disclosures of which are incorporated herein by reference.

FIELD OF THE INVENTION

The present invention relates to a monitoring device for supplementing an injection device configured to eject and dispense a medicament. In particular, the present invention relates to a supplementary device for a manually operable injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

It may be desirable to measure information related to a condition and/or use of the injection device, such as for instance information on the injected insulin type and dose. It may be also desirable to keep track of a dosing history, i.e. about the date and time at which a medicament has been injected. Gathering of such information might be useful to control a patient's compliance with a predefined medication schedule.

Document WO 2013/120775 A1 describes for instance an electronic clip-on module for a manually operable pen-type injection device. The module configured as a supplementary device or monitoring device has a body and a mating unit configured to releasably mount the body to the injection device in a specific position relative to an outside surface of the injection device for a secure and releasable fastening of the supplementary device to the injection device.

Some clip-on modules are attached to an outer circumference of a handheld injection device in such a way that the clip-on module entirely covers a dosage window of the injection device. Dose size indicating information that appears in the dosage window is then exclusively detectable and readable by the clip-on module. The original dosage window of an injection device may be entirely covered. For clip-on devices covering the dosage window a failure safe and a highly reliable functionality must be provided. The technical demands for such clip-on devices with regards to failure safety might be therefore comparatively high in order to meet regulatory demands.

In view of this it would be desirable to have a clip-on module or a monitoring device that avoids a completely covering of a dosage window often injection device and which provides an automated acquisition of dose size information and/or of a dosing history.

SUMMARY

In one aspect there is provided a monitoring device for attachment to an injection device. The monitoring device comprises a body. The body has an inside surface for engagement with an outside surface of the injection device. The body further have an outside surface that is located opposite to the inside surface. Hence, the inside surface and the outside surface are located on opposite sides of form opposite side of the body.

The monitoring device further comprises or defines a light transmission area extending from the inside surface to the outside surface. The light transmission area has an inner end adjacent to the inside surface and further have an outer end that is located adjacent to the outside surface. The light transmission area of the monitoring device provides transmission of light from the inner end to the outer end.

The monitoring device also has an image acquisition system that is arranged inside or on the body. The image acquisition system typically comprises an imaging optics and a light sensitive sensor. By means of the image acquisition system visual information provided on or below the outside surface of the injection device can be acquired.

The monitoring device also has an optical coupling arranged in or adjacent to the light transmission area. The optical coupling is optically coupled to the image acquisition system in a light transmitting way. The optical coupling may be also arranged to reach into or to extend into the light transmission area. The optical coupling may contribute to an edge or a sidewall of the body confining the light transmission area In other words the light transmission area provides transmission of light therethrough. It supports and enables propagation of light from the inside surface to the outside surface of the body. The optical coupling arranged in or extending into the light transmission area provides propagation of light to the image acquisition system. In this way the light transmission area provides a substantiality unobstructed view therethrough. Light reflected from an outside surface of the injection device or light reflected therefrom is now enabled to propagate through the light transmission area of the body. This enables a direct visual view of at least a portion of the outside surface of the injection device. When attached appropriately to the injection device the body of the monitoring device it arranged such that the light transmission area at least partially covers are aligned with a dosage window of the injection device. Dose size related information typically appearing in the dosage window is therefore directly discernible to a user.

In addition and by means of the optical coupling arranged inside or extending into the light transmission area an automated data or image acquisition can be provided to gather visual information from the outside surface of the injection device, in particular from the dosage window of the injection device.

In one example the light transmission area is located in a through opening of the body. The through opening extends from the inside surface to the outside surface of the body.

The light transmission area may also define a through opening of the body and may hence coincide with the through opening. An inside facing sidewall portion of the through opening may be confined by the body. For instance, the through opening comprises a rectangular or circular cross-section.

The through opening may comprise a closed circumference. It may be entirely enclosed and surrounded by the body.

In alternative examples the through opening or the light transmission area may be located at a side edge of the body or may form a side edge of the body. An inside facing sidewall portion of the through opening may then coincide with an outer edge or an outer sidewall portion of the body.

In another example of the optical coupling comprises a mirroring object located between the inner end and the outer end of the light transmission area. In an alternative the mirroring object may also coincide with the outer end or may even form the outer end of the light transmission area. With either example the mirroring object is arranged and configured to deflect light entering the light transmission area through the inner end towards the image acquisition system. The optical coupling may also comprise a diffractive optical element configured to deflect and/or to modify at least one of the shape, the direction or propagation characteristic of light propagating through the light transmission area from the inside surface into the outside surface.

The mirroring object may have outer dimensions that are smaller than an inner cross-section of the light transmission area. In this way and even if the mirroring object should be highly reflective and/or substantially non-transparent the mirroring object would not completely obstruct a look through the light transmission area.

In another example the mirroring object is partially transparent for light in the visible spectral range. For instance, the mirroring object may comprise an optical transmission coefficient of greater than or equal to 0.5, greater than or equal to 0.6, greater than or equal to 0.7 or greater than or equal to 0.8. With a particularly transparent mirroring object the optical coupling may also entirely cover the light transmission area. The optical coupling may thus extend across the entire cross section or diameter of the light transmission area. The partial transparency of the mirroring object would be sufficient to provide a look through the light transmission area and to provide substantiality unhindered or unblocked propagation of light through the transmission area, namely from the inner end towards and through the outer end thereof.

In another example of the mirroring object is aligned substantially parallel to at least one of the inside surface and the outside surface. Here, the mirroring object may be located adjacent to or may coincide with the position of the outer end of the light transmission area. In an alternative the mirroring object is inclined or tilted with regard to at least one of the inside surface and the outside surface. In this way light propagating along a longitudinal axis extending from the inner ends to the outer end of the light transmission area can be deflected towards the image acquisition system. The image acquisition system can be located at a portion or section of the body that is located between the inner end and the outer end. Arranging the mirroring object in an inclined or tilted orientation with regards to the longitudinal axis enables to branch off at least a portion of light propagating from the inner end to the outer end and to direct a branched off portion of the light towards the image acquisition system.

A tilted or inclined arrangement of the mirroring object provides a high degree of flexibility for arranging the image acquisition inside the body.

In another example the mirroring object comprises a mirror or a prism. The mirror may be planar-shaped or may comprise a concave or convex shape. In this way and when implemented as a concave- or convex-shaped mirror the mirroring object may provide a magnification or a focusing of light towards the image acquisition system. When implemented as a prism the mirroring object may provide not only one but several reflections or deflections of light along an optical path from the inner end of the light transmission area towards the image acquisition system. This enables an even greater flexibility and offers further possibilities for arranging the image acquisition system inside the body.

In another example the monitoring device further comprises at least one light source arranged inside the body or attached to the body. The light source is configured to generate and to emit a reading light. The at least one light source is typically configured to provide the reading light propagating through the light transmission area towards and through the inner end thereof. In this way the at least one light source is configured to illuminate an outside surface of the injection device. In particular, the at least one light source may be configured and arranged to illuminate a dosage window of the injection device when the monitoring device is properly connected or attached thereto.

By means of the at least one light source readability of a dosage window located adjacent to the inner end of the light transmission area can be increased, e.g. if a surrounding illumination should not be sufficient for reading of the dosage window by a user for automated image acquisition to be conducted by the image acquisition system. The at least one light source may comprise at least one light emitting diode (LED). Providing and activating of the at least one light source supports and improves a visual perceptibility of a dosage window for a user looking through the light transmission area. Furthermore, the at least one light source also enhances and improves image acquisition conducted by the image acquisition system.

In another example the light source is configured to generate and to emit the reading light in a non-visible spectral range. In addition the image acquisition system comprises a light sensor or that is sensitive to the reading light in the nonvisible spectral range. For instance, image acquisition may be conducted on the basis of infrared light or on the basis of ultraviolet light. Use of a light source in combination with a correspondingly sensitive sensor operating in a non-visible spectral range enables hiding an automated image acquisition from the user of the device. The end-user will not realize that the image acquisition system is actually taking one or several images of the dosage window.

Implementation of the light source and the corresponding light sensor in a non-visible spectral range is of further benefit for that background light in the visible spectral range may then only have a limited or neglectible influence on the process of image acquisition.

In a further example the monitoring device comprises a controller operably connected to the image acquisition system. The controller has a storage to store images captured by the image acquisition system. Alternatively, the storage may be configured to store data obtained or extracted from the image acquisition system or from images captured therewith. The controller may be externally triggered, e.g. by a switch or by a software to capture an image. The controller may be also configured to provide an automated image acquisition. The controller may be configured to constantly monitor an output signal of the image acquisition system.

The controller may be configured to track dynamic changes of captured signals. As soon as the dynamic changes are below a predefined threshold value the controller may trigger capturing of at least one several images by means of the image acquisition system. The predefined threshold value may be characteristic for a steady-state configuration of the dosage window. In typical configurations a user may dial or set a dose of variable size. During setting of the dose numbers appearing in the dosage window are subject to a continuous modification. As soon as two or more consecutive images taken by the image acquisition system are substantially identical this might be considered as an indication that the process of dose setting has terminated.

By monitoring consecutive images taken by the image acquisition system the controller may be further operable to determine whether the process of dose setting has terminated or whether the process of dose setting continues after an interruption. Hence, the controller may be configured to compare the content of subsequent images acquired at consecutive instants of time. A comparison of the content of subsequently acquired images may be evaluated by the controller in order to determine if a dose setting procedure is still in progress or if a dose setting procedure has terminated and/or if a dose dispensing procedure is currently taking place.

In another example the controller is operably connected to the at least one light source. The controller is then further configured to trigger an admission of the reading light via the light source by means of the light source. In particular, the controller is configured to trigger the at least one light source and the image acquisition system concurrently or simultaneously. In this way the light source is only activated at such time instants at which the image acquisition system is recording an image. Such a concurrent activation of the image acquisition system and the at least one light source is of particular use when the light source operated in a non-visible spectral range. A selective activation of the light source on demand and controlled via the controller provides and enables electrical energy saving.

With a further example the controller comprises an optical character recognition engine (OCR) configured to recognize the symbols or numbers in an image captured by the image acquisition system. In this way the controller is enabled and configured extract and information content from an acquired images. In this way it is only required that the storage of the controller is configured to store data rather than entire images. In this way storage space and a storage capacity of the storage can be reduced.

In another example the light transmission area is confined by at least one sidewall extending from the inner end to the outer end. The sidewall comprises at least one beveled section extending towards a transverse midsection of the light transmission area and towards the outer end. A transverse midsection is located at a predefined distance from the sidewall of the light transmission area. The term "transverse" denotes a direction perpendicular to the longitudinal axis of the light transmission area. With examples wherein the light transmission area comprises a cylindrically-shaped through opening the transverse direction corresponds to a radial direction with regard to the cylindrical shape. With other geometries of a through opening defining or coinciding with the light transmission area the transverse midsection is located in the transverse middle of the through opening.

The beveled section of the sidewall may be located near or adjacent to the outer end. With a circular symmetric or cylindrically shaped through opening the beveled section may extend radially inwardly towards the outer end. The beveled section may provide an inwardly extending overhang. A surface of the beveled section may be partially reflective and may act and behave as the mirroring object. Alternatively the mirroring object may be arranged in or at the beveled section. The beveled section extending at a predefined angle with regard to the longitudinal axis of the light transmission area may thus provide a desired deflection of light towards the image acquisition system.

In another aspect an injection system is provided comprising an injection device and further comprising a monitoring device as described above which is configured for attachment to a housing of the injection device such that the light transmission area of the monitoring device is aligned with a dosage window of the injection device. Typically, the injection device is configured for setting and dispensing of a dose of a medicament, e.g. of a liquid medicament. The injection device has an elongated housing with a dosage window to visualize dose-size related information. The housing comprises at least an outside surface to which the monitoring device can be attached.

The injection device may comprise a handheld injection device. It may comprise or may be configured as a pen-type injection device. The injection device may be configured as a mechanically implemented injection device with an analog dosage window. Inside the housing of the injection device there may be provided a number sleeve having printed numbers on an outer circumference. The number sleeve may be rotationally supported inside the housing so that an increasing or a decreasing sequence of numbers appears in the dosage window during setting of a dose and/or dispensing of a dose of the medicament.

Typically, the injection device comprises a drive mechanism featuring at least a piston rod or a plunger to apply pressure onto a bung or a piston of a cartridge that is filled with the medicament. In this way an amount of the medicament, hence a dose of the medicament can be expelled through a distal end of the cartridge. The distal end of the cartridge is typically sealed with a pierceable seal, such as a rubber septum. For injecting or dispensing of a dose of the medicament the pierceable seal is penetrable by a double-tipped injection needle, which is typically releasably attachable to a dispensing end of the injection device, e.g. to a distal end of a cartridge holder of the housing of the injection device.

The monitoring device and the injection device comprise mutually corresponding fastening features. The monitoring device may comprise at least one or several snap features by way of which a snap fit connection of the monitoring device and the injection device can be provided. There may be provided specific protrusions, ribs or indentations on the outside surface of the injection device to mate with correspondingly-shaped protrusions, ribs or indentations on the inside surface of the body of the monitoring device. In addition or alternatively the body of the monitoring device may be fastened to the outside surface of the housing of the injection device by way of friction. For this the inside surface of the body of the monitoring device may be provided with a friction enhancing finish, e.g. with a rubber pad.

The body of the monitoring device may comprise any desired or arbitrary shape. It may comprise an annular shape with an inner open diameter that is large enough to receive the housing of the injection device there through. The body and hence the entire monitoring device may enclose the entire outer circumference of the housing of the injection device. With other examples the body of the monitoring device comprises a semicircular or arched shape, an oval or somewhat rectangular shape. It may be configured for fastening to only one lateral side of the housing of the injection device, typically to that side of the housing that is provided with the dosage window.

In another example the injection device comprises a cartridge that is at least partially filled with a medicament. The cartridge is arranged inside the injection device. In this way the injection device may be provided as a prefilled injection device. The injection device may be configured and designed as a disposable injection device, which after use or consumption of the medicament located in its cartridge is intended to be discarded in its entirety. In another example the injection device may be configured as a re-usable injection device, wherein a cartridge holder section of the housing of the injection device is detachable from a main housing section so as to replace an empty cartridge by a new one.

In a further aspect there is provided a method of capturing a dose of a medicament set or dispensed with an injection device. The method comprises the steps of:
 providing an injection device configured for setting and dispensing of a dose of a medicament and having an elongated housing with an outside surface and with a dosage window to visualize dose size related information,
 providing of a monitoring device configured for capturing an image of the dosage window and/or for capturing information appearing in the dosage window of the injection device,
 arranging the monitoring device to the injection device and aligning a light transmission area of the monitoring device with the dosage window,
 capturing of an image of the dosage window with an image acquisition system of the monitoring device and
 providing a visual appearance of at least a part of the dosage window through the light transmission area.

Typically, the monitoring device comprises a body with an inside surface and an outside surface located opposite to the inside surface. The body of the monitoring device further comprises a light transmission area with an inner end adjacent to the inside surface and with an outer end adjacent to the outside surface. The light transmission area provides transmission of light from the inner end to the outer end. In particular, the light transmission area provides entering of light through the inner end, propagation of light through the light transmission area and emission of light through and beyond the outer end.

The monitoring device also comprises an image acquisition system arranged inside or on the body. The monitoring device further comprises an optical coupling arranged in or adjacent to the light transmission area, wherein the optical coupling is optically coupled to the image acquisition system Typically, the monitoring device to be used with the above-mentioned method is a monitoring device as described above. The method of capturing a dose of the injection device is beneficial in that an image or information of the dosage window of the injection device can be automatically captured by the monitoring device and that a user of the device is simultaneously provided with a rather direct and unobstructed view of the dosage window.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as it is defined by the claims. Further, it is to be noted, that any reference numerals used in the appended claims are not to be construed as limiting the scope of the invention.

BRIEF DESCRIPTION OF THE DRAWINGS

In the following various embodiments of a data collection device in connection with an injection device are described by making reference to the drawings, in which.

DETAILED DESCRIPTION

Figure 1:
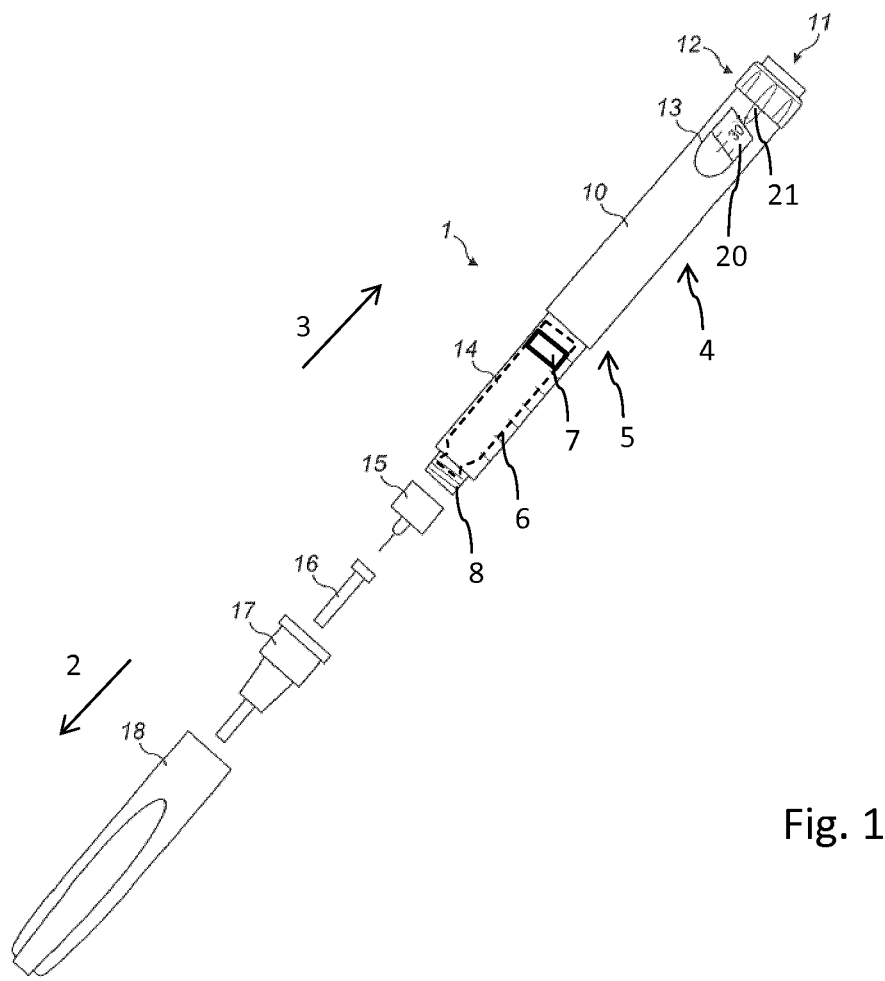
FIG. 1 is a schematic view of a handheld injection device.

FIG. 1 shows an example of a handheld injection device 1. The injection device 1 comprises an elongated housing. The housing comprises a main housing component 10 and a cartridge holder 14. The main housing component 10 is located at a proximal end of the injection device 1. The cartridge holder 14 is located at a distal or at a dispensing end of the injection device 1. Inside the cartridge holder 14 there is provided a cartridge 6 that is filled with a liquid medicament. The cartridge 6 comprises a cylindrical or tubular shaped barrel that is sealed in proximal direction 3 by a bung 7 or piston. The bung 7 is displaceable in distal direction 2 by means of a piston rod that is driven by the drive mechanism 4 of the injection device 1.

The injection device 1 further comprises a dose setting mechanism 5 allowing and supporting setting of a dose of the medicament. The dose setting mechanism 5 comprises a dose dial 12 located at a proximal end of the main housing component 10. The dose dial 12 is rotatable in a dose incrementing direction, e.g. clockwise so as to set a dose of desired size. The injection device 1 further comprises a trigger 11 located at the proximal end of the injection device 1. The trigger 11 comprises a dose button that is depressible in distal direction 2, typically, by a thumb of a user.

Towards the distal and dispensing end the injection device 1, e.g. the cartridge holder 14 is provided with a threaded socket 8. There is further provided a needle assembly 15 typically comprising a needle hub and a double-tipped injection needle. The needle hub and hence the needle assembly 15 is releasably attachable to the distal end of the cartridge holder 14. Typically, the needle hub comprises an inner thread that mates with an outer thread of the threaded socket 8. The injection needle is typically covered and protected by an inner needle cap 16. The entire needle assembly 15 may be protected by an outer needle cap 17 that is configured to receive both, the needle assembly 15 and the inner needle cap 17. The injection device 1 is further provided with a protective cap 18 configured to cover the distal end of the injection device 1. The protective cap 18 is particularly configured to receive the cartridge holder 14. The protective cap 18 may be snap fitted to the cartridge holder 14 or to the main housing component 10.

The injection device 1 further comprises a dosage window 13. In the illustrated example the dosage window 13 is located near a proximal end of the injection device 1. The dosage window 13 is shown in greater detail in FIG. 2. The dosage window 13 may comprise a through opening in a sidewall of the main housing component 10. The dosage window 13 may comprise a transparent cover to prevent ingress of dust or humidity into the main housing component 10. The main housing component 10 comprises an outside surface 19 that is configured for attachment or connection with a monitoring device 50. Below the dosage window 13 and inside the main housing component 10 there is typically provided a number sleeve 20 having a series of numbers printed thereon. The number sleeve 20 is rotationally supported inside the housing 10. It may be threadedly engaged with an inside facing sidewall portion of the main housing component 10. A rotation of the number sleeve 20 may come along with a translational displacement of the number sleeve 20 relative to a longitudinal axis of the main housing component 10.

Figure 2:
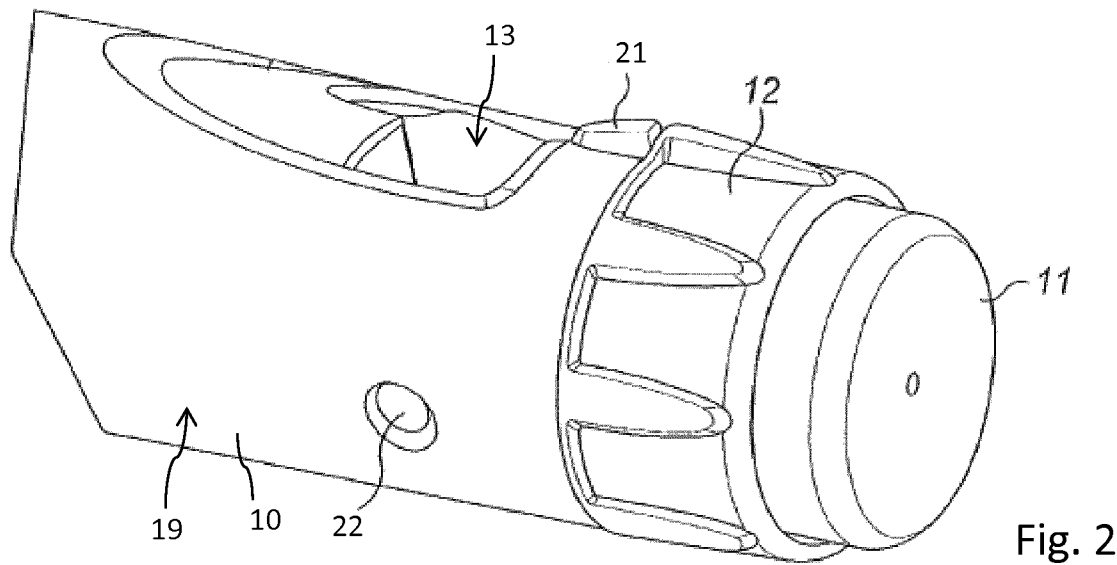
FIG. 2 is an enlarged perspective view of a proximal end of the injection device of FIG. 1, FIG. 3 it an exemplary embodiment of the monitoring device, FIG. 4 it a schematic side view of the monitoring device attached to the injection device.

As it is further shown in FIG. 2, a rib 21 protrudes from the outer surface 19 of the injection device 1 that acts as an alignment element for locating the monitoring device 50 in a specific position relative to the outside surface 19 of the injection device 1.

Figure 3:
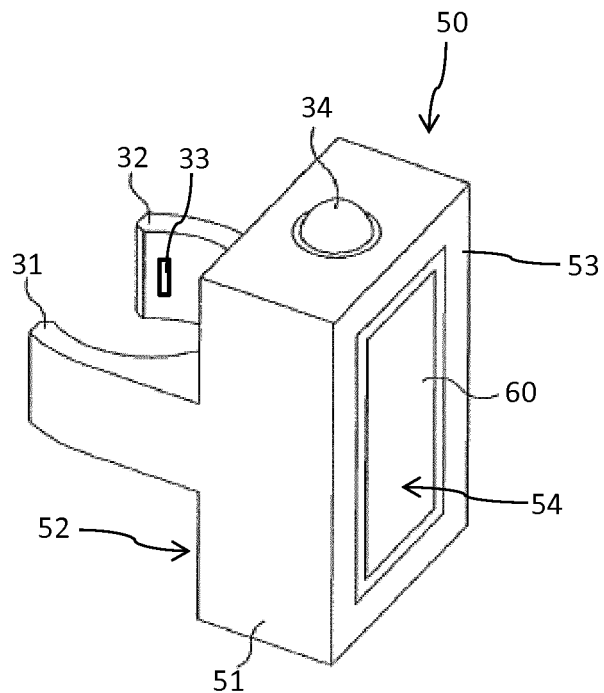

In FIG. 3 an example of a monitoring device 50 is illustrated. Here, the monitoring device 50 comprises a body 51 with an outside surface 53 and an inside surface 52. The monitoring device 50 further comprises a first and a second connector 31, 32 that protrude from the inside surface 52. The first and the second connectors 31, 32 are configured as fastening clips. They are arranged at a distance from each other that roughly matches the diameter of the tubular-shaped main housing component 10. As illustrated in FIG. 2, the main housing component 10 may not only comprise radially outwardly protruding ribs 21 but may also have at least one indentation 22 on the outside surface 19. The at least one indentation 22 mates with an inside facing portion of the connectors 31, 32. The connectors may be provided with correspondingly-shaped protrusions 33 of which only a protrusion 33 is shown in FIG. 3. When appropriately mounted and attached to the injection device the protrusion 33 may snap into the indentation 22 and may thus positively engage with the main housing component 10. In this way a well-defined attachment of the monitoring device 50 to the injection device 1 can be provided.

When mounted to the injection device 1 the monitoring device 50 obstructs the dosage window 13. In order to provide a direct view of the dosage window 13 through the monitoring device 50 the monitoring device 50 comprises a light transmission area 60. With the example of FIG. 3 the light transmission area 60 comprises a through opening 54 extending through the body 51 from the inside surface 52 to the outside surface 53. The light transmission area 60 and hence the through opening 54 therefore provides a substantially unobstructed view of the dosage window 13 when the monitoring device 50 is attached to the injection device 1.

In addition to the light transmission area 60 the monitoring device 50 further comprises an image acquisition system 70 that acquires an image of a portion of the number sleeve 20 that is visible through the dosage window 13. In addition and as shown in FIG. 3 the monitoring device 50 may further comprise a trigger 34, e.g. in form of at least one button that is depressible by a user in order to conduct an image acquisition or a data communication with an external electronic device.

Figure 6:
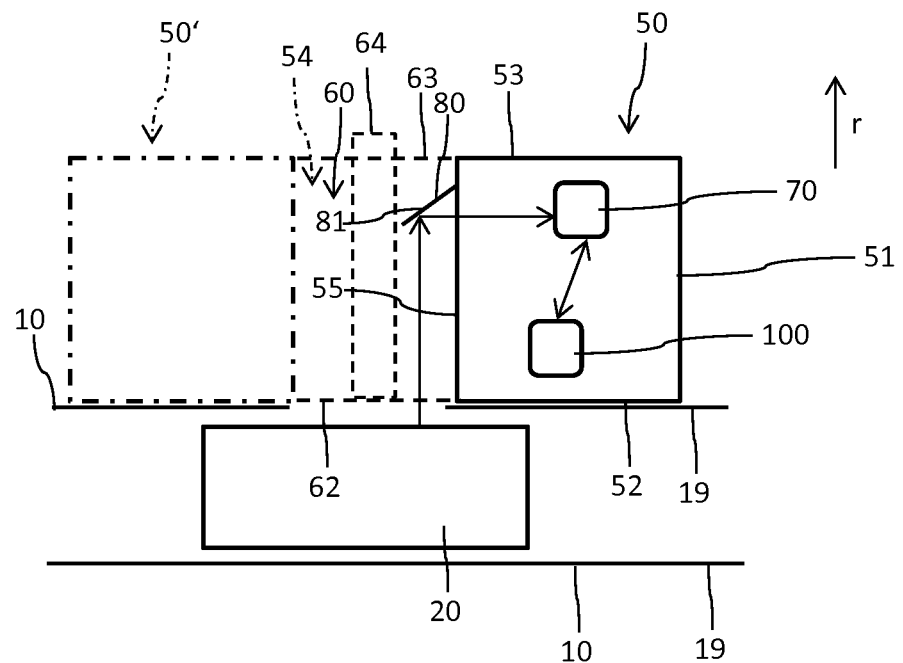

A more detailed view of the interaction between the monitoring device 50 and the injection device 1 is shown in FIG. 6. The monitoring device 50 is attached to an outside surface 19 of the injection device 1. The body 51 of the monitoring device 50 has an inside surface 52 that is in engagement or in abutment with the outside surface 19 of the injection device 1. The light transmission area 60 extends from the inside surface 52 to the outside surface 53. In the example as illustrated in FIG. 6 the light transmission area 60 is located axially adjacent to the body 51. It is confined in axial direction, hence along the longitudinal axis of the injection device 1, by a sidewall 55 of the body 51. The sidewall 55 has an extension along a radial direction r with regards to the tubular or cylindrical geometry of the main housing component 10. The light transmission area 60 is confined by an inner end 62 shown as dotted line in FIG. 6 and by an outer end 63, also shown as a dotted line. The inner end 62 flushes with the inside surface 52. The outer end 63 flushes with the outside surface 53. Hence, the inner end and the outer end 62, 63 are axial extensions of the inside surface 52 and the outside surface 53, respectively.

Inside the light transmission area 60 there is provided an optical coupling 80. In the example of FIG. 6 the optical coupling 80 comprises a mirroring object 81 in form of a plane-shaped mirror. The mirroring object 81 is inclined compared to the longitudinal extension of the light transmission area 60, which in the example of FIG. 6 extends radially outwardly. The inclination of the mirroring object 81 is about 45° with regards to the longitudinal axis of the injection device 1. It may be also inclined by about 45° with respect to the radial direction r. As illustrated in FIG. 6 a light beam 9 propagating outwardly from the number sleeve 20 and through the dosage window 13 impinges on the mirroring object 81 and is deflected or redirected towards the image acquisition system 70 located inside the body 51. In the example of FIG. 6 the mirroring object 81 is at least partially located outside the body 51. It may extend out of the body 51 or may protrude from the body 51. It may be also integrated into a sidewall of the body 51. The mirroring object 81 may extend into the light transmission area 60 in order to branch off at least a portion of the light 9 reflected by or emanating from the dosage window 13. In FIG. 6 there is also illustrated an axial midsection 64 of the light transmission area 60. The axial midsection is located at a distance to the sidewall 55 confining the light transmission area 60.

In FIG. 6 there is further shown a second body 51' in dash-dotted lines. This second body 51' is only optional and represents an example of the monitoring device 50 wherein the light transmission area is formed by a through opening 54 extending through the body 51 of the monitoring device. Hence, the body 51 and the body 51' our integrally formed and belong to one and the same body. In such an example the light transmission area 60 is completely enclosed by the sidewall 55 of the through opening 54. The monitoring device 50 can be attached to the main housing component 10 in a way as already described in connection with FIGS. 2 and 3 or by means of any other type of fastening means.

Figure 4:
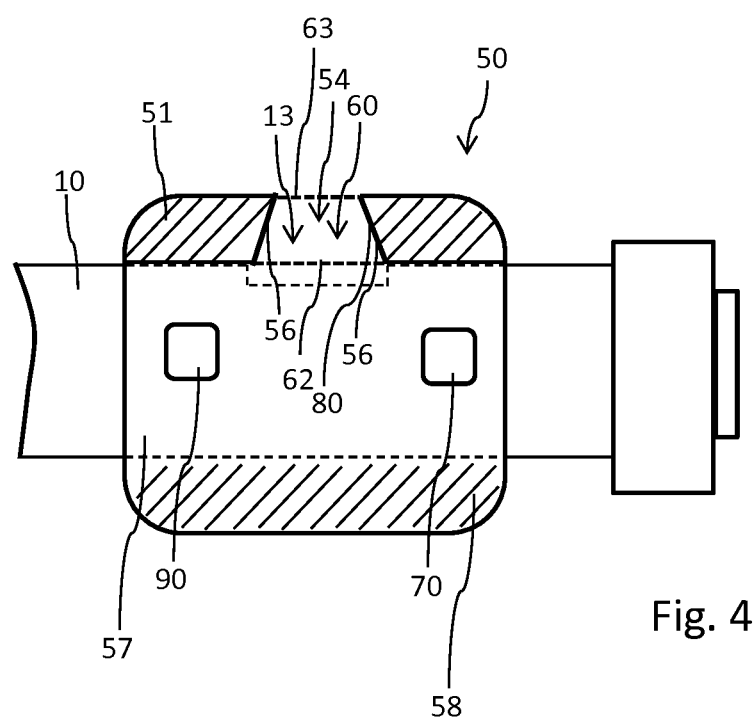

In FIG. 4, another example of a monitoring device 50 is shown. Here, the body 51 comprises an annular or sleeve-like shape with an outer diameter and an inner diameter. The inner diameter is sized to fit around the outer circumference of the injection device 1. It is releasably attachable to the injection device 1 by means of mutually engaging fastening features, such as indentations 22 and/or protrusions 33 provided on the outside surface 19 of the injection device 1 and on an inside surface of the body 51.

As shown in cross-section in FIG. 4, the light transmission area 60 is provided inside a through opening 54 through the body 51. When attached appropriately to the injection device 1 the light transmission area 60 is arranged across or over the dosage window 13 so as to provide an unobstructed view of the dosage window 13 and to a portion of the number sleeve 20 that is visible through the dosage window 13

As indicated in FIG. 4 the sidewall 55 of the through opening 54 comprises a beveled section 56 close to or adjacent to the outer end 63 of the light transmission area 60. Here, the beveled section 56 is provided with the optical coupling 80. By means of the beveled section 56 or by means of several diametrically oppositely located beveled sections 56 light generated by a light source 90 located in a first portion 57 of the body 51 may propagate through the beveled section 56 towards and onto the dosage window 13. From there reflected light may propagate towards an oppositely located beveled section 56 located at or in a second portion 58 of the body 51. Here, the image acquisition system is located in the second portion 58 of the body 51.

As shown in FIG. 4, the first portion 57 and the second portion 58 are located on opposite sides of the light transmission area 60. When the monitoring device 50 is mounted to the injection device 1 the beveled sections 56 are located at opposite axial portions of the dosage window 13. Accordingly, the light source 90 and the image acquisition system 70 are located at opposite longitudinal ends or axial edges of the dosage window 13 of the injection device 1.

Figure 5:
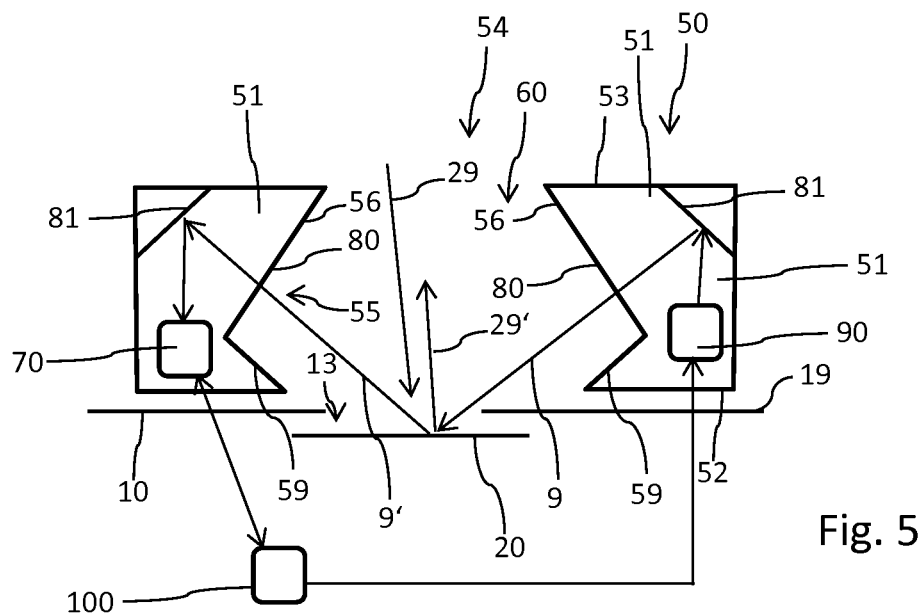
FIG. 5 is a schematic illustration of light propagating in the monitoring device, FIG. 6 it is a schematic illustration of the monitoring device when attached to the injection device.

In FIG. 5, a similar example of a monitoring device 50 is conceptually illustrated. There, a sidewall 55 of the light transmission area 60 comprises two oppositely inclined beveled sections 56, 59. As seen from the inside surface 52 or inner end 62 towards the outside surface 53 or towards the outer end 63 the beveled section 59 extends away from the midsection 64 of the light transmission area 60 whereas the adjacently located beveled section 56 extends inwardly or towards the midsection 64. With an inwardly beveled section 56 near or adjacent to the outside surface 53 light generated from the light source 90 can be coupled into the light transmission area 60 at a well-defined radial distance from the dosage window 13. A diverging light beam may thus homogeneously illuminate the dosage window 13.

When having the optical coupling 80 in the region of the beveled section 56 which is located at a certain distance from the dosage window 13 imaging of the dosage window 13 is facilitated compared to a configuration in which there is limited space between on object to be imaged and the position of an optical image thereof. The demands for an imaging optics can be thus reduced. The image acquisition system 70 may comprise a diffractive optical element, such as a Fresnel lens providing an image of the dosage window 13 or of a portion of the number sleeve 20 at comparatively small image distance. This is rather beneficial for achieving a miniaturization of the monitoring device 50 and of the image acquisition system 70.

In the embodiment of FIG. 5 the optical coupling 80 is integrated into the sidewall 55 of the through opening 54 provided in the body 51. Here, the optical coupling 80 provides transmission through the sidewall 55. It is hence configured to transfer and to couple light 9 from a light source 90 out of the body 51 and into the light transmission area 60 as well as to couple light 9' reflected by the number sleeve 20 or by the dosage window 13 back into the body 51.

The optical coupling 80 further comprises a mirroring object 81, e.g. in form of a plane mirror. Here, the mirroring object 81 is positioned and arranged inside the body 51. It is inclined at a predefined angle so as to direct light emitted by the at least one light source 90 through the optical coupling 80 in the beveled section 56 of the sidewall 55 and towards the dosage window 13. A portion of the light 9' reflected from the number sleeve 20 or from the dosage window 13 then impinges on an oppositely located sidewall portion 55 and enters into the body 51 through another optical coupling 80 located in another beveled section 56. There, the reflected light 9' is reflected by a further mirroring object 81 from which it is deflected and reflected to the image acquisition system 70.

In addition the light transmission area 60 is completely unobstructed. In this way ambient light 29 may enter the light transmission area 60 from outside. Ambient light may be reflected by the number sleeve 20 or by the dosage window 13 and may propagate in a substantially opposite direction as reflected light 29'. With this example the artificial light 9 generated by the at least one light source 90 will hardly leave the light transmission area 60 via its outer end 63. Since the light source 90 and the image acquisition system 70 are arranged axially offset from the dosage window 13 the light 9 emanating from the light source 90 propagates at a predefined angle relative to the axis of elongation of the injection device 1. The artificial light 9 generated by the at least one light source 90 will not hinder or deteriorate the readability and discernability of the dosage window 13 through the light transmission area 60.

In addition or as an alternative the light 9 generated by the light source 90 may be in a nonvisible spectral range. The automated reading or image acquisition of the number sleeve 20 will be hardly discernible to the end user or patient.

In the example of FIG. 5 there is also shown a controller 100. The controller 100 comprises at least a storage 100 to store images captured by the image acquisition system 70 or to store extracted data from images taken and provided by the image acquisition system 70. The controller 100 may be further coupled and connected to the light source 90. The controller 100 may be configured to concurrently trigger an image acquisition conducted by the image acquisition system 70 and to emit light from the light source 90. Light emitted from the light source 90 may be directed into the light transmission area 60 through the optical coupling 80, e.g. integrated into a sidewall 55 of the body 51. Here, the optical coupling may comprise a transparent window.

Figure 7:
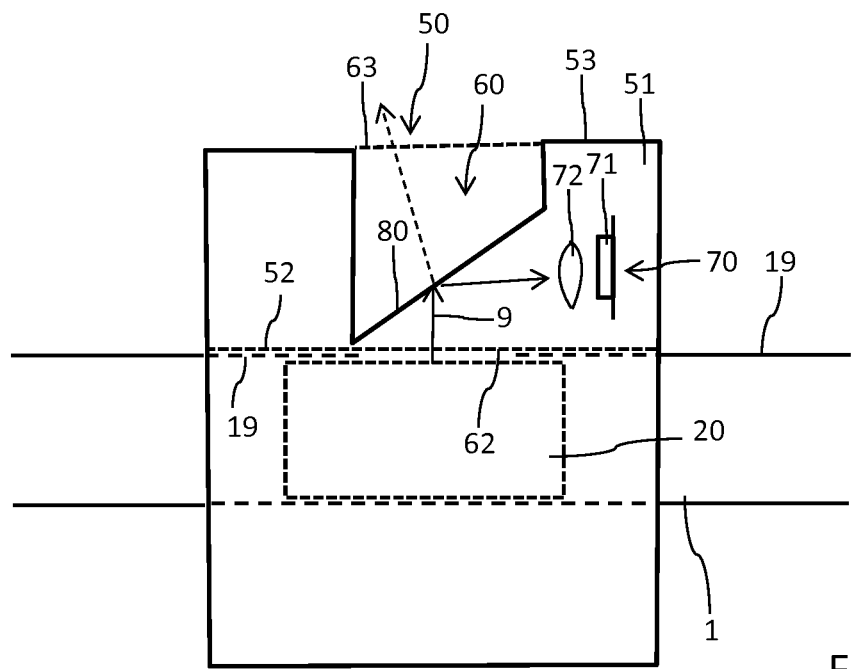
FIG. 7 shows another example of the monitoring device when attached to the injection device, FIG. 8 it is illustrative of another example of the monitoring device.

FIG. 7 is illustrative of another example of the monitoring device 50. Here, the optical coupling 80 in the form of a partially transparent mirror is arranged across the entire light transmission area 60. As further illustrated in FIG. 7 the mirroring object 81, hence a plane shaped partially transparent mirror is inclined relative to the longitudinal extension of the injection device 1. As shown in FIG. 7, the angle of inclination is about 45°. It may range between 30° and 60°. As shown in FIG. 7, light 9 reflected by or emanated from the number sleeve 20 and propagated through the dosage window 13 is partially reflected and deflected by an inside surface of the mirroring object 81. A portion of the light propagating into the inner end 62 is branched off and is directed towards the image acquisition system 70 comprising a light sensor 71 and a lens 72. The lens 72 may comprise a refractive lens 72 or a diffractive optical element.

Another portion of the light 9 is propagating through the mirroring object 81. It is visible by a user of the device 1 who is thus capable to take a direct and undistorted view of the dosage window 13.

Figure 8:
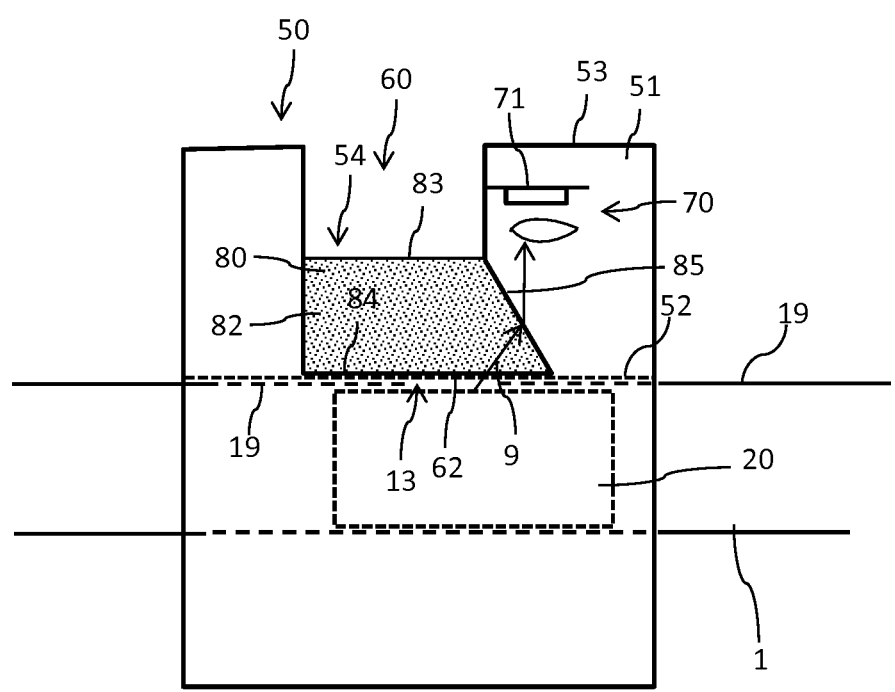

In the example according to FIG. 8 the optical coupling 80 comprises a prism 82 having an outside surface 83 and an oppositely located inside surface 84 and an inclined side surface 85. The inclined surface 85 provides a reflection of the light 9 propagating from the dosage window 13 into the light transmission area 60 and into the prism 82. The inclined surface 85 provides a deflection of light 9 entering and propagating through the prism 82. Here, the orientation of the image acquisition system 70 differs from the orientation of the image acquisition system 70 as shown in FIG. 7. In FIG. 7 the image acquisition system is oriented longitudinally, hence along the main axis or longitudinal axis of the injection device 1. In FIG. 8, the optical axis of the image acquisition system 70 is rotated by 90° compared to the configuration of FIG. 7. In FIG. 8 the optical axis of the image acquisition system 70 is arranged and oriented radially with regards to the cylindrical shape of the injection device 1.

Figure 9:
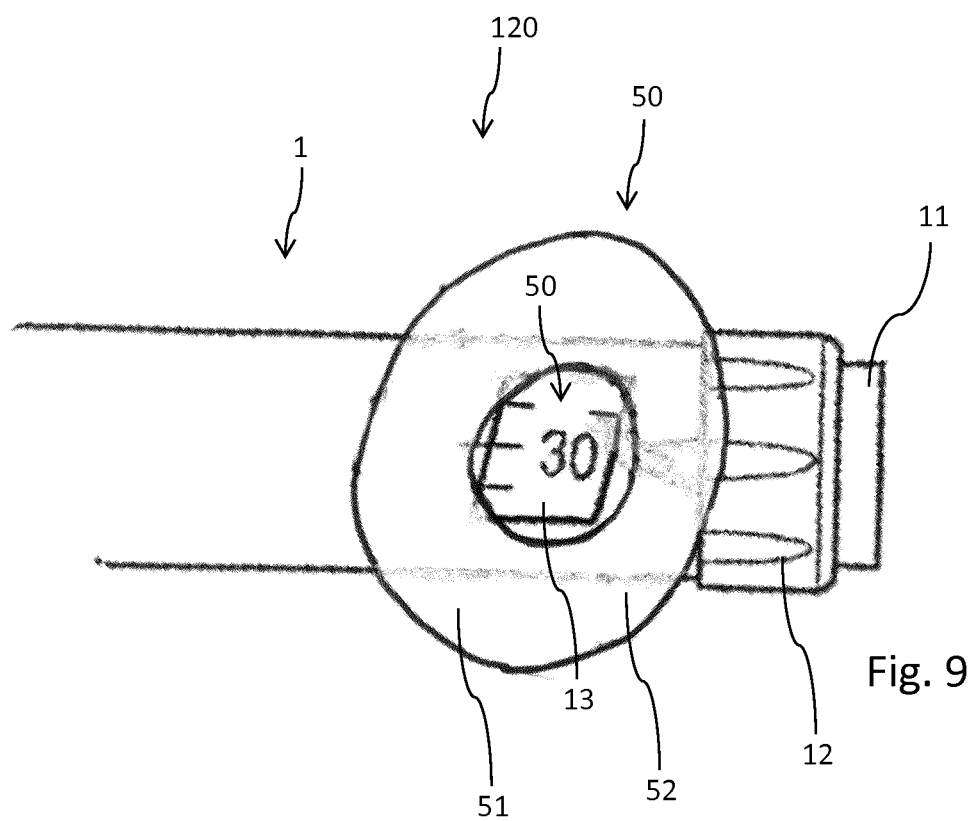
FIG. 9 is illustrative of a front view of the monitoring device when attached to the injection device.

In FIG. 9, a top view of an injection system 120 comprising the injection device 1 and the monitoring device 50 is provided. Here, the light transmission area 60 of the body 51 of the monitoring device 50 comprises a circular-shaped through opening 54 through the body 51 so as to provide an unobstructed and/or undistorted view of the dosage window 13 that is entirely obstructed and covered by the monitoring device 50 when the monitoring device 50 is properly arranged and aligned on the outside surface 19 of the injection device 1.

Figure 10:
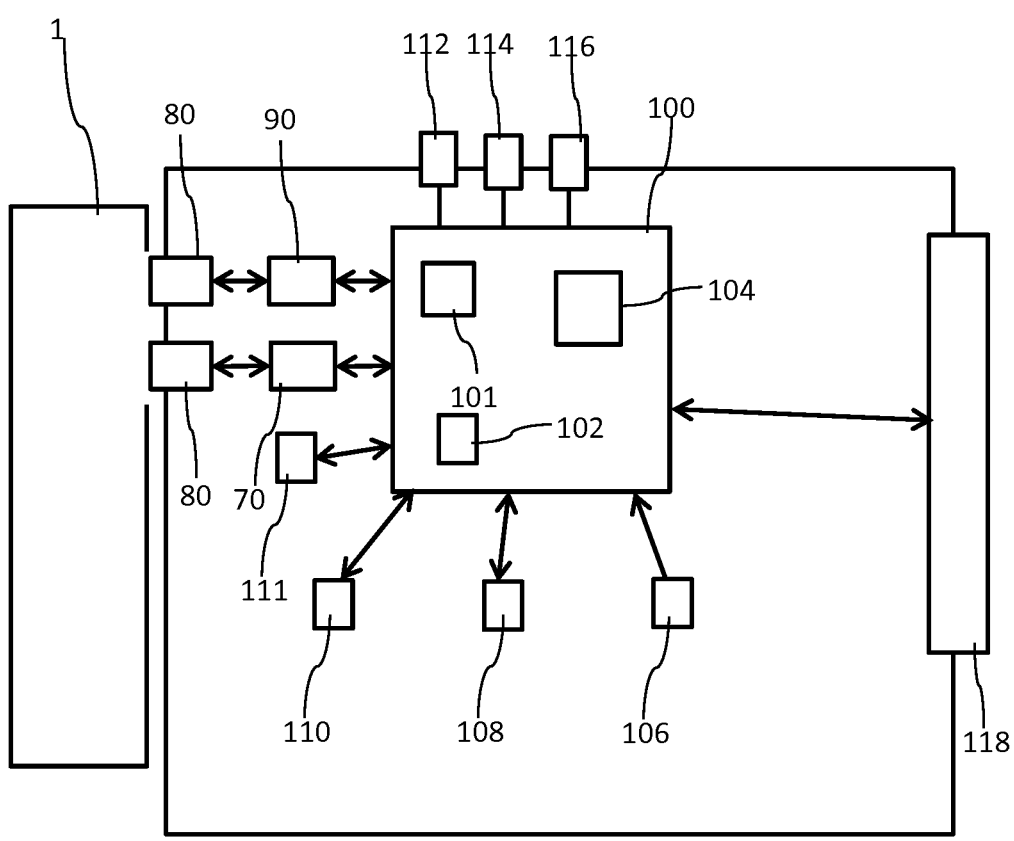
FIG. 10 shows a block diagram of the monitoring device when attached to the injection device.

FIG. 10 is further illustrative of a block diagram of the monitoring device 50. The monitoring device 50 comprises a controller 100, which may for instance comprise a processor 104 in form of a Digital Signal Processor (DSP), Application Specific Integrated Circuit (ASIC), Field Programmable Gate Array (FPGA) or the like. The controller 100 and the processor 104 execute program code (e.g. software or firmware) stored in a program memory 101. The controller 100 may further comprise and/or use a storage 102 as a main memory, for instance to store intermediate results or to store acquired images or data extracted therefrom. The storage 102 may also be used to store a logbook on performed ejections/injections. The program memory 101 may for instance be a Read-Only Memory (ROM), and main memory may for instance be a Random Access Memory (RAM).

In an example embodiment, controller 100 interacts with a first button 112, via which the monitoring device 50 may for instance be turned on and off. A second button 114 can be implemented as a communications button. The second button 112 may be used to trigger establishment of a connection to another device, or to trigger a transmission of information to external electronic device. A third button 116 is a confirm or OK button.

The third button 116 can be used to acknowledge information presented to a user of monitoring device 50. The buttons 112, 114, 116, 33, 34 may be any suitable form of user input transducers, for instance mechanical switches, capacitive sensors or other touch sensors.

The controller 100 may optionally control a display unit 118, which is presently embodied as a Liquid Crystal Display (LCD). The display unit 118 is used to display information to a user of the monitoring device 50, for instance on present settings of the injection device 1, or on a next injection to be given. The display unit 118 may also be embodied as a touch-screen display, for instance to receive user input.

The controller 100 it is operatively connected and coupled to the image acquisition system 70. The image acquisition system 70 comprises an optical sensor 71. This sensor 71 can be embodied as an Optical Character Recognition (OCR) reader, that is capable of capturing images of the dosage display 13, in which a currently selected dose is displayed by way of numbers printed on the sleeve 20 contained in injection device 1, which numbers are visible through the dosage display 13. The OCR reader implemented by the image acquisition system 70 and/or the controller 100 is further capable of recognizing characters (e.g. numbers) from the captured image and to provide this information to the processor 104. Alternatively, the image acquisition system 70 may only be an optical sensor, e.g. a camera, for capturing images and providing information on the captured images to controller 100. Then, the controller 100 is responsible for performing OCR on the captured images.

The controller 100 also controls at least one light-source 90 such as at least one light emitting diode (LEDs) to illuminate the dosage display 13, in which a currently selected dose is displayed. A diffuser may be used in front of the light-source, for instance, a diffuser made from a piece of acrylic glass. Furthermore, the optical sensor 71 may comprise a lens (e.g. an aspheric lens) leading to a magnification (e.g. a magnification of more than 3:1)

Controller 100 further controls (and/or receives signals from) an acoustic sensor 111, which is configured to sense sounds produced by injection device 1. Such sounds may for instance occur when a dose is set by turning the dose dial 12 and/or when a dose is ejected/injected by pressing the trigger 11, and/or when a prime shot is performed. These actions are mechanically similar but nevertheless sound differently (this may also be the case for electronic sounds that indicate these actions). Either the sensor 111 and/or the controller 100 may be configured to differentiate these different sounds, for instance to be able to safely recognize that an injection has taken place (rather than a prime shot only).

The controller 100 further controls an acoustical a signal generator 110, which is configured to produce acoustical and/or optical signals that may for instance be related to the operating status of injection device 1, for instance as feedback to the user. For example, an acoustical signal may be launched by the signal generator 110 as a reminder for the next dose to be injected or as a warning signal, for instance in case of misuse. The signal generator may for instance be embodied as a buzzer or loudspeaker. In addition, the signal generator 110 may comprise and/or include a haptic signal generator that may provide haptic feedback, for instance by way of vibration.

The controller 100 further controls a wireless unit 108, which is configured to transmit and/or to receive information to or from another external electronic device in a wireless fashion. Such transmission may for instance be based on radio transmission or optical transmission. In some embodiments, the wireless unit 108 is a Bluetooth transceiver. Alternatively, the wireless unit 108 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

A power supply 106, e.g. in form of a battery, powers the controller 100 and other components by way of a power supply. The monitoring device 50 of FIG. 10 is thus capable of determining information related to a condition and/or use of injection device 1. This information is displayed on the display 118 for use by the user of the injection system 120. The information may be either processed by the monitoring device 50 itself, or may at least partially be provided to another external electronic device (e.g. a blood glucose monitoring system).

Figure 11:
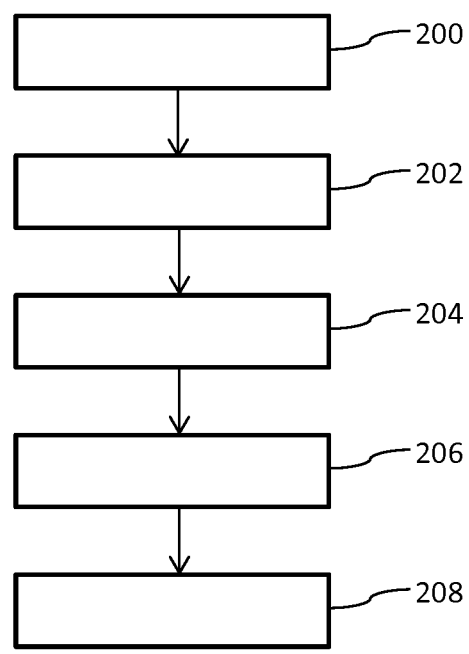
FIG. 11 is a flowchart of a method for capturing an image of a dosage window of an injection device.

In FIG. 11 a flowchart of a method of capturing a dose size set or dispensed by an injection device 1 is shown. There, in step 200 an injection device configured for setting and dispensing of a dose of a medicament is provided. The injection device has an elongated housing 10 with an outside surface 19 and with a dosage window 13 to visualize dose size related information. In a next step 202 a monitoring device 50 is provided. The monitoring device 50 is configured to capture an image of the dosage window 13 and/or to capture information appearing in the dosage window 13 of the injection device 1.

In a further step 204 the monitoring device 50 is arranged to the injection device 1. The monitoring device 50 is arranged to the injection device 1 in such a way that a light transmission area 60 of the monitoring device 50 at least partially covers the dosage window 13. In an attachment configuration the elongation of the light transmission area 60 extends in radial direction with regard to a cylindrical or tubular shape of the housing 10 of the injection device 1. In this way the light transmission area 60 is aligned with the dosage window 13. In a next step 206 an image of the dosage window 13 is captured with the image acquisition system 70 of the monitoring device 50.

Simultaneous to the capturing of the image in step 208 the monitoring device provides a visual appearance of at least a part of the dosage window 13 through and beyond the light transmission area 60.

LIST OF REFERENCE NUMBERS 1 injection device
2 distal direction
3 proximal direction
4 drive mechanism
5 dose setting mechanism
6 cartridge
7 bung
8 threaded socket
9 light
10 main housing component
11 trigger
12 dose dial
13 dosage window
14 cartridge holder
15 needle assembly
16 inner needle cap
17 outer needle cap
18 protective cap
19 outside surface
20 number sleeve
21 rib
22 indentation
29 ambient light
31 connector
32 connector
33 protrusion
34 trigger
50 monitoring device
51 body
52 inside surface
53 outside surface
54 through opening
55 sidewall
56 beveled section
57 first portion
58 second portion
59 beveled section
60 light transmission area
62 inner end
63 outer end
64 midsection
70 image acquisition system
71 light sensor
72 lens
80 optical coupling
81 mirroring object
82 prism
83 outside surface
84 inside surface
85 surface
90 light source
100 controller
101 program memory
102 storage
104 processor
106 power supply
108 wireless unit
110 signal generator
111 sensor
112 button
114 button
116 button
118 display unit
120 injection system

The invention claimed is:

1. A monitoring device for attachment to an injection device, the monitoring device comprising:
a body comprising:
an inside surface configured for engagement with an outside surface of the injection device; and
an outside surface opposite to the inside surface;
a light transmission area extending from the inside surface of the body to the outside surface of the body, the light transmission area comprising:
an inner end adjacent to the inside surface of the body;
an outer end adjacent to the outside surface of the body;
wherein the light transmission area is configured to provide transmission of light from the inner end of the light transmission area to the outer end of the light transmission area;
an image acquisition system arranged inside or on the body; and
an optical coupling arranged in or adjacent to the light transmission area, wherein the optical coupling is optically coupled to the image acquisition system.

2. The monitoring device of claim 1, wherein the light transmission area is located in a through opening of the body and wherein the through opening extends from the inside surface of the body to the outside surface of the body.

3. The monitoring device of claim 1, wherein the optical coupling comprises a mirroring object located between the inner end of the light transmission area and the outer end of the light transmission area or coinciding with the outer end of the light transmission area, and wherein the mirroring object is arranged and configured to deflect light entering the light transmission area through the inner end of the light transmission area towards the image acquisition system.

4. The monitoring device of claim 3, wherein the mirroring object is partially transparent for light in the visible spectral range.

5. The monitoring device of claim 3, wherein the mirroring object extends across an entire cross section of the light transmission area.

6. The monitoring device of claim 3, wherein the mirroring object is aligned substantially parallel to at least one of the inside surface of the body or the outside surface of the body, or wherein the mirroring object is inclined to at least one of the one of the inside surface of the body or the outside surface of the body.

7. The monitoring device of claim 3, wherein the mirroring object comprises a mirror or a prism.

8. The monitoring device of claim 1, further comprising at least one light source arranged inside the body and configured to generate and to emit a reading light.

9. The monitoring device of claim 8, wherein the at least one light source is configured to generate and to emit the reading light in a non-visible spectral range, and wherein the image acquisition system comprises a light sensor that is sensitive to the reading light.

10. The monitoring device of claim 1, further comprising a controller operably connected to the image acquisition system and comprising a storage to store image data captured by the image acquisition system.

11. The monitoring device of claim 10, further comprising at least one light source arranged inside the body and configured to generate and to emit a reading light, wherein the controller is operably connected to the at least one light source and configured to:
- trigger an emission of the reading light via the at least one light source; and
- trigger an image acquisition of light entering the transmission area through the inner end.

12. The monitoring device of claim 1, wherein the light transmission area is confined by at least one sidewall extending from the inner end of the light transmission area to the outer end of the light transmission area, and wherein the sidewall comprises a beveled section extending towards a transverse midsection of the light transmission area and towards the outer end of the light transmission area.

13. An injection system, comprising:
- an injection device configured for setting and dispensing of a dose of a medicament, the injection device comprising an elongated housing, the elongated housing comprising:
  - a dosage window to visualize dose size related information; and
  - an outer surface; and
- a monitoring device comprising:
  - a body comprising:
    - an inside surface configured for engagement with the outer surface of the housing; and
    - an outside surface opposite to the inside surface;
  - a light transmission area extending from the inside surface of the body to the outside surface of the body, the light transmission area comprising:
    - an inner end adjacent to the inside surface of the body;
    - an outer end adjacent to the outside surface of the body;
  - wherein the light transmission area is configured to provide transmission of light from the inner end of the light transmission area to the outer end of the light transmission area;
  - an image acquisition system arranged inside or on the body; and
  - an optical coupling arranged in or adjacent to the light transmission area, wherein the optical coupling is optically coupled to the image acquisition system,
  - wherein the monitoring device is configured for attachment to the housing of the injection device such that the transmission area is aligned with the dosage window.

14. The injection system of claim 13, further comprising a cartridge at least partially filled with the medicament and being arranged inside the injection device.

15. The injection system of claim 13, wherein the light transmission area is located in a through opening of the body and wherein the through opening extends from the inside surface of the body to the outside surface of the body.

16. The injection system of claim 13, wherein the optical coupling comprises a mirroring object located between the inner end of the light transmission area and the outer end of the light transmission area or coinciding with the outer end of the light transmission area, and wherein the mirroring object is arranged and configured to deflect light entering the light transmission area through the inner end of the light transmission area towards the image acquisition system.

17. The injection system of claim 16, wherein the mirroring object is partially transparent for light in the visible spectral range.

18. The injection system of claim 16, wherein the mirroring object extends across an entire cross section of the light transmission area.

19. The injection system of claim 16, wherein the mirroring object is aligned substantially parallel to at least one of the inside surface of the body or the outside surface of the body, or wherein the mirroring object is inclined to at least one of the one of the inside surface of the body or the outside surface of the body.

20. A method of capturing a dose of a medicament set or dispensed with an injection device, the method comprising:
- arranging a monitoring device to the injection device;
- aligning a light transmission area of the monitoring device with a dosage window of the injection device;
- capturing an image of the dosage window with an image acquisition system of the monitoring device; and
- providing a visual appearance of at least a part of the dosage window through the light transmission area.

* * * * *